United States Patent
Lechner-Greite et al.

(10) Patent No.: US 10,076,249 B2
(45) Date of Patent: Sep. 18, 2018

(54) PROTON DENSITY AND T1 WEIGHTED ZERO TE MR THERMOMETRY

(71) Applicant: GENERAL ELECTRIC COMPANY, Schenectady, NY (US)

(72) Inventors: Silke Maria Lechner-Greite, Ismaning (DE); Florian Wiesinger, Freising (DE); Desmond Teck Beng Yeo, Clifton Park, NY (US); Matthew Richard Tarasek, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 640 days.

(21) Appl. No.: 14/817,450

(22) Filed: Aug. 4, 2015

(65) Prior Publication Data
US 2017/0035301 A1 Feb. 9, 2017

(51) Int. Cl.
*A61B 5/00* (2006.01)
*A61B 5/01* (2006.01)
*G01R 33/48* (2006.01)
*G01R 33/56* (2006.01)
*A61B 18/18* (2006.01)
(Continued)

(52) U.S. Cl.
CPC ............ *A61B 5/015* (2013.01); *A61B 5/4836* (2013.01); *A61B 5/7214* (2013.01); *A61B 5/7285* (2013.01); *G01R 33/4804* (2013.01); *G01R 33/4816* (2013.01); *A61B 18/02* (2013.01); *A61B 18/04* (2013.01); *A61B 18/1815* (2013.01); *A61B 2018/00577* (2013.01); *A61B 2018/00791* (2013.01); *G01R 33/4814* (2013.01); *G01R 33/5602* (2013.01)

(58) Field of Classification Search
CPC ..... A61B 5/015; A61B 5/4836; A61B 5/7214; G01R 33/4804; G01R 33/4816
See application file for complete search history.

(56) References Cited

U.S. PATENT DOCUMENTS

| 5,910,728 A | 6/1999 | Sodickson |
| 6,032,068 A | 2/2000 | Daniel et al. |

(Continued)

FOREIGN PATENT DOCUMENTS

DE    19952965 A1    5/2001

OTHER PUBLICATIONS

Goldhaber, D.M. et al.,"Measurement of tissue temperature by MRI", Nuclear Science Symposium and Medical Imaging Conference, 1993., 1993 IEEE Conference Record, vol. 3, pp. 1702-1705, San Francisco, CA, Oct. 31-Nov. 6, 1993.

(Continued)

*Primary Examiner* — Joseph M Santos Rodriguez
(74) *Attorney, Agent, or Firm* — GE Global Patent Operation; Pabitra Chakrabarti (57) ABSTRACT

A system and method for tracking temperature changes in tissue and bone is disclosed. In one aspect, the temperature changes are tracked simultaneously with high spatial encoding and temporal efficiency. The method is robust in terms of B0 and chemical shift off-resonance, as well as insensitive to eddy currents for accurate temperature mapping. Zero TE (ZTE) based MR thermometry is utilized herein to extract temperature changes from proton density and T1 weighted images. Additionally, T1 signal contamination is corrected for by calibrating T1 and B0 by using a variable flip angle method to achieve temperature mapping in bone, aqueous and adipose tissue simultaneously.

17 Claims, 7 Drawing Sheets

(51) Int. Cl.
  *A61B 18/00* (2006.01)
  *A61B 18/02* (2006.01)
  *A61B 18/04* (2006.01)

(56) References Cited

U.S. PATENT DOCUMENTS

| | | |
|---|---|---|
| 7,211,055 B2 | 5/2007 | Diederich et al. |
| 7,344,530 B2 | 3/2008 | Bischof et al. |
| 8,024,025 B2 | 9/2011 | Mallozzi et al. |
| 8,326,010 B2 | 12/2012 | Hofstetter et al. |
| 8,655,038 B2 | 2/2014 | Keereman et al. |
| 2011/0196224 A1 | 8/2011 | Stehing et al. |
| 2013/0200900 A1 | 8/2013 | Buurman et al. |
| 2013/0274592 A1 | 10/2013 | Shin et al. |
| 2013/0335083 A1 | 12/2013 | Wasserman et al. |
| 2015/0080705 A1 | 3/2015 | Partanen et al. |

OTHER PUBLICATIONS

Jing et al.,"Investigation of proton density for measuring tissue temperature", Journal of Magnetic Resonance Imaging vol. 23, Issue: 3, pp. 430-434, Mar. 2006.

Shah et al.,"Measuring the Absolute Water Content of the Brain Using Quantitative MRI", Magnetic Resonance Neuroimaging, Methods in Molecular Biology, vol. 711, pp. 29-64, Dec. 15, 2010.

Du J et al.,"Qualitative and quantitative ultrashort-TE MRI of cortical bone", NMR in Biomedicine, vol. 26, Issue: 5, pp. 489-506, Dec. 28, 2012.

Ramsay et al.,"Temperature-dependent MR signals in cortical bone: Potential for monitoring temperature changes during high-intensity focused ultrasound treatment in bone", Magnetic Resonance Annual, Oct. 13, 2014.

PROTON DENSITY AND T1 WEIGHTED ZERO TE MR THERMOMETRY

FIELD

Embodiments relate generally to the field of imaging and more particularly to noninvasive temperature monitoring with magnetic resonance (MR) imaging.

BACKGROUND

Many non-invasive or minimal-invasive therapies (such as MR-guided high intensity focused ultrasound (HIFU) or radio frequency (RF) deep hyperthermia) require accurate temperature monitoring in the human body. MR-based temperature mapping in tissue is performed using the temperature-dependent proton resonance frequency shift (PRFS) phenomenon, the diffusion coefficient (D), the longitudinal ($T_1$) and transversal ($T_2$) relaxation times, proton density (PD), magnetization transfer, as well as temperature sensitive contrast agents. In particular, the PRFS method is commonly used for MR thermometry (MRT) because it is a simple and robust MRT method in water-based tissues. $T_1$ based thermal mapping in combination with a variable flip angle (VFA) method is used to track temperature changes in adipose tissue. Relative temperature changes in tissue and fat can also be measured by leveraging the temperature-dependent PD signal.

Some of the thermal therapies have to be performed very close to bony structures; or energy used for the treatment has to be transmitted through bone. The potential risk of bone heating makes it highly desirable to further acquire temperature updates in bone for accurate treatment monitoring, which is not clinically performed yet. Cortical bone, as well as other bony structures, have ultra-short $T_2$ relaxation properties (i.e. $T_2$<1 milliseconds), which requires dedicated acquisition techniques to capture the rapidly decaying MR signals with appropriate signal-to-noise ratio (SNR). Examples of existing methods that perform MRT in or around bone include: a dual-echo single slice two dimensional (2D) spoiled gradient echo sequence for simultaneous tracking of temperature change in bone and cerebral tissue; the normalized change of signal magnitude of the short echo time images is used to extract the temperature change of bone. The long-echo time images provide phase information and temperature changes are extracted based on the PRFS method for soft tissue. Nevertheless, high SNR is utilized, whereas with this method, only 20% of SNR could be achieved; a three dimensional (3D) ultra-short echo time (UTE) sequence to evaluate $T_1$ changes due to heating in cortical bone and $T_2$ changes in yellow bone marrow; UTE imaging to compensate for phase-aberrations in the skull; combined UTE with spectroscopic imaging (UTESI) to monitor temperature changes in the musculoskeletal system; and qualitative and quantitative results of UTE-based MRT of cortical bone.

Recently, zero echo time (ZTE) MR bone imaging in the head has been introduced as a technology in multi-modality diagnostic imaging. The echo time (TE) of an MRI sequence is considered zero when the generation of the transverse magnetization coincides with the acquisition of the k-space center. This feature is characteristic for ZTE techniques with the 3D radial readout gradient active during excitation. For example, PD weighted images are acquired using e.g. the rotating ultra-fast imaging sequence (RUFIS) to extract bone structures used for image segmentation. ZTE features a non-selective hard pulse excitation together with 3D center-out radial sampling with the spokes arranged on a spiral path requiring minimal gradient ramping in between repetitions. The PD weighting is achieved by using very small flip angles. Applying a variable flip angle method, ZTE allows for an efficient $T_1$ mapping, too. A limitation of using the temperature-dependent PD signal to measure temperature changes in tissue, where PD weighting is imperfect or has to be compromised, is the $T_1$ signal dependency influencing the PD weighted signal resulting in signal contrast changes and hence incorrect temperature map calculations. Perfect PD weighting is achieved in the limiting case of a flip angle (FA)→0 and TR→infinity. Hence, this limitation could be overcome by increasing the repetition time (TR), which prolongs the total acquisition time to a point that makes the PD weighted temperature mapping impossible for applications that need a temperature update every few seconds.

The present method will address the issues as detailed above. The method will desirably provide a technique for MRT to measure temperature changes in MR-visible tissues based on PD and T1 weighted ZTE for accurate treatment monitoring.

SUMMARY

The system and method of the invention pertains to a method which extracts temperature changes from PD and T1 weighted images acquired with zero echo time (ZTE) imaging. Additionally, $T_1$ and $B_1$ may be calibrated using a variable flip angle method based on ZTE to achieve signal-to-noise ratio optimized PD and T1 weighted ZTE temperature maps.

Embodiments disclosed herein describe a method of mapping and tracking temperature changes using magnetic resonance imaging (MRI) of MRI-visible tissues by leveraging the effect of proton density (PD) and longitudinal relaxation time (T1) weighting including T1 and radio frequency field strength (B1) correction to perform temperature mapping, the method comprising the steps of: generating a plurality of images with PD and T1 weighting by adjusting flip angles and repetition times (TR) to produce a series comprising one or more PD weighted images, PD and T1 weighted images, and signal-to-noise (SNR)-optimized T1 weighted images that are indicative of temperature information within different layers of MRI-visible tissues; calibrating T1 signal contamination from the series comprising the one or more PD weighted ZTE images, PD and T1 weighted images, and signal-to-noise (SNR)-optimized T1 weighted images; and extracting temperature changes from the series comprising the one or more PD weighted images, PD and T1 weighted images, and signal-to-noise (SNR)-optimized T1 weighted images to map and track temperature changes in the MRI-visible tissues. The plurality of images can be acquired with zero echo time (ZTE) acquisitions, or by other known methods including UTE, among others.

During the step of calibrating T1 signal contamination, the steps include determining a T1 calibration map from a T1 monitoring region of interest, re-calibrating the T1 calibration map and repeatedly updating the T1 calibration map by applying a T1 mapping sequence. The T1 mapping sequence can be a zero echo time (ZTE) pulse sequence based variable flip angle (VFA) calibration method that produces one or more of the series. A step of calibrating T1 signal contamination may also comprise the steps of determining a B1 calibration map, re-calibrating the B1 calibration map, and repeatedly updating the B1 calibration map by applying a B1 mapping sequence. The B1 mapping sequence may be a ZTE pulse sequence based variable flip angle (VFA) calibration method that produces one or more of the series, or any sequence as known in the art.

The method may be implemented to visualize any MRI-visible tissues including bone, aqueous and adipose tissues. The MRI-visible tissues also include bone compositions comprising bone marrow, cortical bone, and trabecular bone.

In addition, during the step of generating a plurality of ZTE pulse sequences, the image acquisition performed in three dimensional (3D) space, and silently. Generating the plurality of ZTE sequences is insensitive to geometric distortions and eddy currents to accurately map temperature in the MRI-visible tissues.

Further, the method comprises implementing thermal therapy guidance techniques, including methods of hyperthermia comprising radiofrequency (RF) ablation, laser ablation, high-intensity focused ultrasound (HIFU), infrared, microwave, magnetic and induction heating. Hypothermal therapy may also be utilized such as cryotherapy, comprising passive and active cooling therapies such as cryo-ablation.

The disclosure herein simultaneously tracks temperature changes in bone, aqueous and adipose tissue with high spatiotemporal efficiency. The method is robust in terms of $B_0$ and chemical shift off-resonance, and insensitive to eddy currents, as indicative for accurate temperature mapping. The sequence is silent so that patient comfort is increased during long treatment sessions. Zero TE can be introduced as a simultaneous and simplified single modality treatment planning method to replace time consuming CT scan registration. Zero TE is an effective method for PD weighted imaging and highly SNR efficient. The temperature map extraction is simplified, no phase unwrapping is needed, and ZTE is insensitive to motion during acquisition. Finally, in contrast to some of the non-invasive or minimally invasive thermal therapies that utilize information about location and geometry of bones within the treatment area or the path of the energy transmission, current therapy planning techniques use co-registered computer tomography (CT) images to assess this information.

Embodiments disclosed herein include a method of mapping and tracking temperature changes using magnetic resonance imaging (MRI) of MRI-visible tissues by leveraging the effect of proton density (PD) and T1 weighting including longitudinal relaxation time (T1) and radio frequency field strength (B1) correction, where PD and T1 weighting is obtained by using (but not limited to) either PD or T1-weighted ZTE acquisitions (or combinations thereof). The method comprises the steps of: generating a plurality of PD weighted ZTE pulse sequences with adjusted low flip angles and repetition times (TR) to produce a series of PD weighted ZTE images that are indicative of temperature information within different layers of MRI-visible tissues; and extracting temperature changes from the PD weighted ZTE images.

In one embodiment, a plurality of ZTE pulse sequences are generated with PD and T1 weighting, achieved by adjusting flip angles and repetition times (TR) to produce a series of PD or T1 weighted ZTE images that are indicative of temperature information for MRI-visible tissues; and extracting temperature changes from the PD and T1 weighted ZTE images. For PD weighted ZTE temperature mapping, T1 saturation is accounted for. For T1 weighted ZTE temperature mapping, the relative temperature change is directly calculated from T1.

One embodiment determines a longitudinal relaxation time (T1) and a radio-frequency field strength (B1) calibration map of at least a first temperature monitoring region of interest; generating a plurality of signal-to-noise ratio (SNR) optimized T1 weighted ZTE pulse sequences with adjusted flip angles and TR to produce a series of SNR-optimized T1 weighted ZTE images that are indicative of temperature information for MRI-visible tissues; and extracting temperature changes from the T1 weighted ZTE images where T1 saturation is corrected for using pre-calibrated T1 and B1 maps.

During the step of acquiring the T1 map, the T1 map is calibrated and repeatedly updated by applying any T1 mapping sequence to generate at least one T1 map. In the step of acquiring the B1 map, the B1 map is calibrated and repeatedly updated by applying any known B1 mapping sequence, in particular a ZTE pulse sequence based VFA calibration method to generate at least one B1 map; wherein the step of acquiring the T1 and B1 map is repeated during the cause of experiments to increase accuracy.

The embodiments of the method as described herein may be utilized alone or in combination, and modified in series or combination to further improve ZTE-based MR thermometry.

DETAILED DESCRIPTION

Various embodiments will be better understood when read in conjunction with the appended drawings. It should be understood that the various embodiments are not limited to the arrangements and instrumentality shown in the drawings.

For spoiled gradient echo sequences, the steady-state signal is formulated as:

$$y = \frac{(1 - E1)E2 \sin\alpha}{1 - \cos\alpha E1} M \quad [1]$$

with $$E1 = \exp\left(\frac{-TR}{T1}\right), \ E2 = \exp\left(\frac{-TE}{T2^*}\right),$$

M is the thermal equilibrium magnetization, TR is the repetition time, $T_1$ is the longitudinal relaxation time, $T_2^*$ is the effective transverse relaxation time, and a is the flip angle. For exemplary purposes, and not limitation, approximations are introduced. The following statements are valid for equation [1] also.

For ZTE sequences with zero nominal echo time TE (TE<<$T_2^*$), short repetition times (TR<<$T_1$) and small flip angles ($\alpha$<<1), above equation can be approximated as:

$$y = \frac{\alpha M}{1+\beta} \qquad [2]$$

$$\text{with } \beta = \frac{T1}{TR}\frac{\alpha^2}{2} \qquad [3]$$

According to these equations, temperature changes can be measured in multiple different ways:

Exploring the Proton Density Effect:

The thermal equilibrium magnetization M is temperature dependent according to:

$$M = \frac{M0T0}{(T0+\Delta T)} \approx M0\left(1-\frac{\Delta T}{T0}\right) \qquad [4]$$

with M0 the thermal equilibrium magnetization at temperature T0 and $\Delta T$ the temperature change. Hence, for this measurement, $\beta$ should be kept negligible (i.e. $\beta$<<1) by using small flip angles and/or long repetition times.

ZTE provides the advantage that it is presumably the most efficient method for acquiring proton density weighted images.

Exploring the Proton Density and T1 Effect:

$$T1 = T10 + m\Delta T \qquad [5]$$

with T10 as the longitudinal relaxation time at temperature T0 and 'm' as the T1 temperature coefficient.

ZTE permits efficient T1 mapping using the so-called variable flip angle method. According to equation [2], and for example, two ZTE data sets with different flip angles $\alpha 1$ and $\alpha 2$, M0 and T1 can be extracted from which relative temperature changes are calculated.

SNR-Optimized T1 Weighted ZTE Imaging with Pre-Calibrated T1 and B1 Mapping:

Accounting for both dependencies the signal equation [1] gets:

$$y = \frac{\alpha M0\left(1-\frac{\Delta T}{T0}\right)}{1 + \frac{T10 + m\Delta T}{TR}\frac{\alpha^2}{2}} \qquad [6]$$

which can be resolved for the unknown temperature change $\Delta T$ according to:

$$\Delta T = \frac{\alpha M0 - y(1+\beta)}{\frac{M0}{T0} + \frac{my}{T10}\beta} \qquad [7]$$

By calibrating T10 and $\beta$ at temperature T0, the temperature change can immediately be extracted from the measured signals.

The calibration of accurate T10 maps additionally requires an accurate representation of the achieved radiofrequency field strength (B1) which determines the actual flip angle. Hence, B1 mapping using any known B1 mapping technique, or in particular ZTE based B1 mapping is performed.

Figure 1:
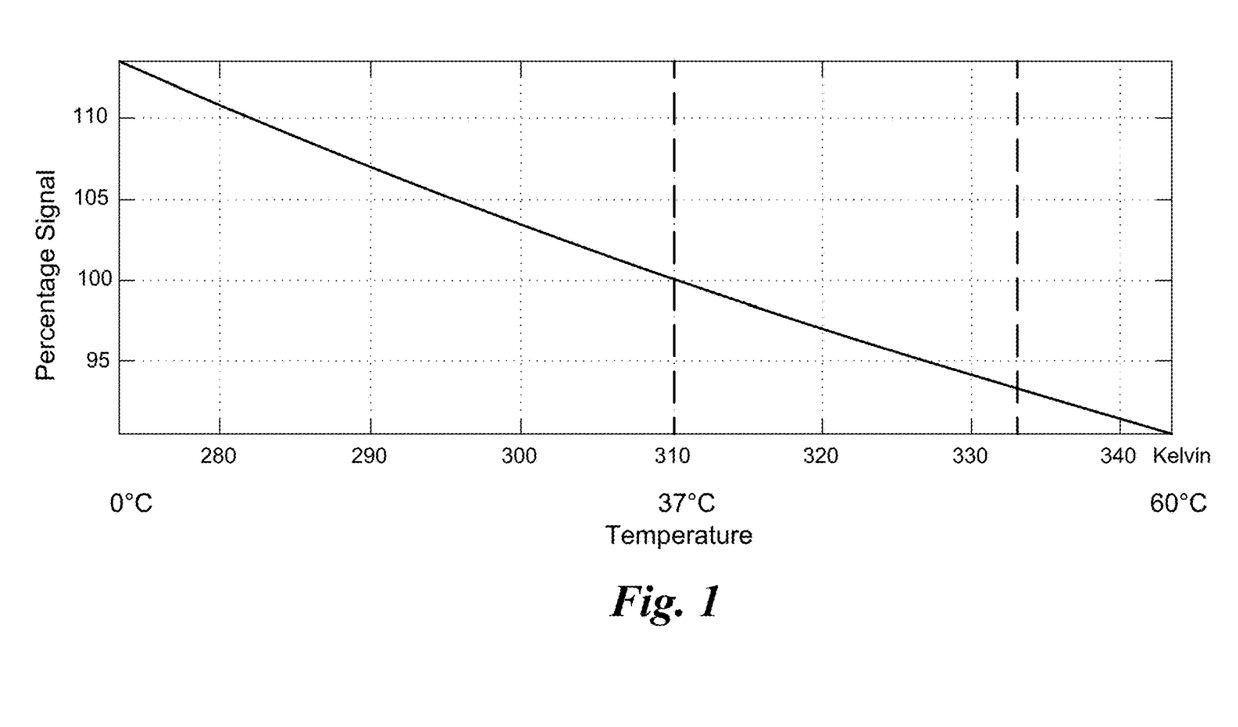
FIG. 1 graphically depicts the temperature sensitivity of the proposed method by illustrating the percentage signal relative to the signal at body temperature.

According to the Boltzmann distribution and Curie law, the magnetization $M_0$ depends on the Boltzmann thermal equilibrium, where the susceptibility is inversely proportional to the absolute temperature 1/T (FIG. 1). At body temperature and a SNR of about 100, a temperature accuracy of about +/−3° C. is expected. For exemplary purposes, an SNR of 300 would achieve a temperature accuracy of 1° C., and so forth.

Figure 2:
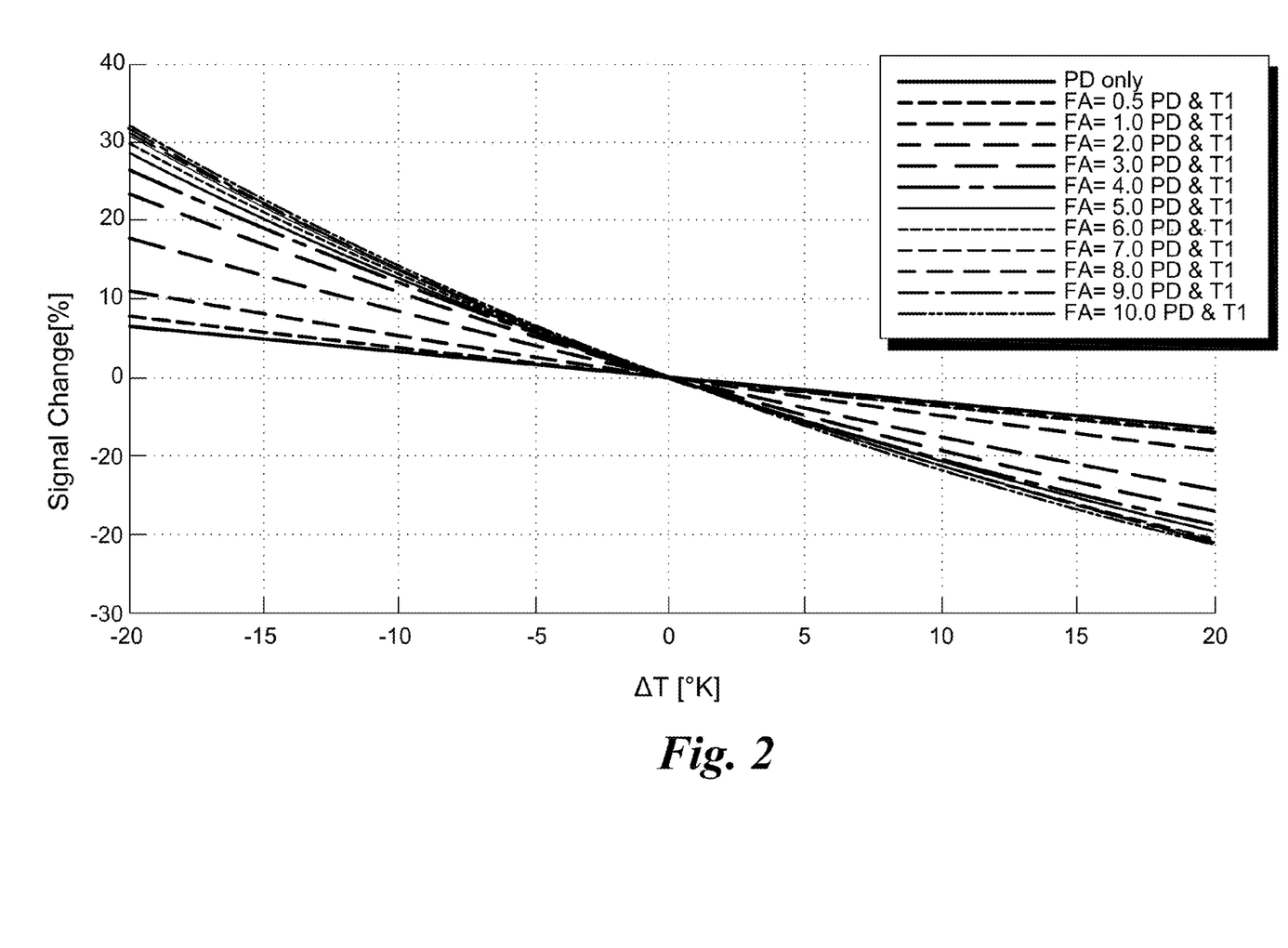
FIG. 2 demonstrates the signal increase when considering T1 contamination in proton density (PD) weighted zero echo time (ZTE) imaging versus PD weighted ZTE imaging alone.

For SNR-optimized T1 weighted ZTE imaging with pre-calibrated T1 and B1 mapping, the temperature sensitivity, as expressed in percent (%) signal change of PD versus T1 weighted ZTE, may be increased by up to about 360% (relative to the PD effect) when selecting a flip angle between about 4 to 10° (as shown in FIG. 2). This leads to a higher accuracy of temperature measurement. FIG. 2 depicts T1 weighted ZTE, combining the PD and T1 temperature effect, to increase temperature sensitivity. By applying the SNR-optimized T1 weighted ZTE imaging with pre-calibrated T1 and B1 mapping, temperature changes with high spatiotemporal resolution and accuracy are extracted. Various flip angles are depicted in FIG. 2.

The temperature change can be measured in multiple ways: (i) PD weighted ZTE imaging, (ii) PD and T1 weighted ZTE imaging, and (iii) SNR-optimized T1 weighted ZTE imaging with pre-calibrated T1 and B1 mapping.

Figure 3:
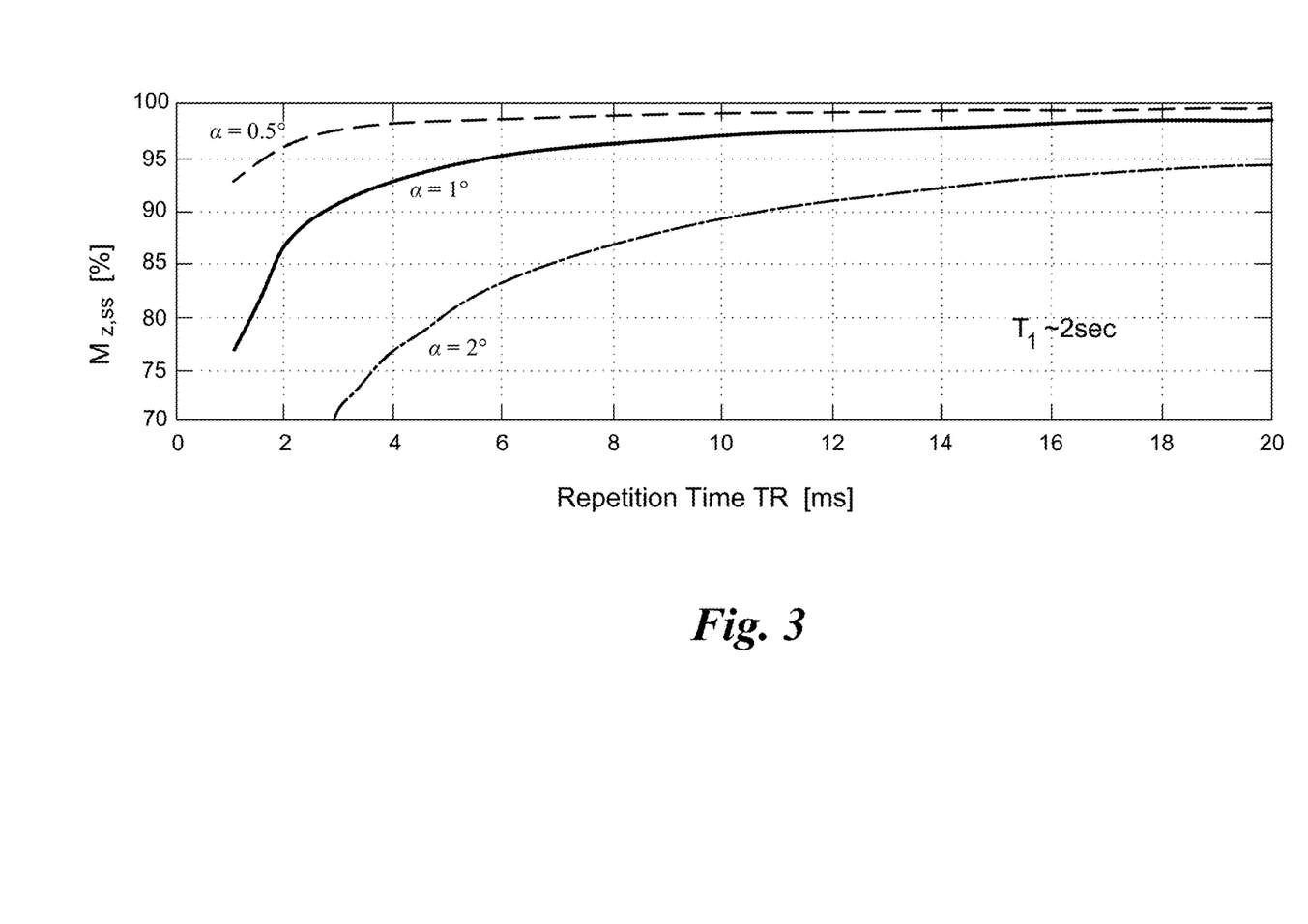
FIG. 3 demonstrates proton density weighting and steady state considerations for different flip angles.

As shown in FIG. 3, PD weighting is achieved by setting a flip angle close to about 0.5° so that a thermal equilibrium magnetization in steady state (M0) reaches greater than about 90% for TR times of about 2 ms.

Figure 4:
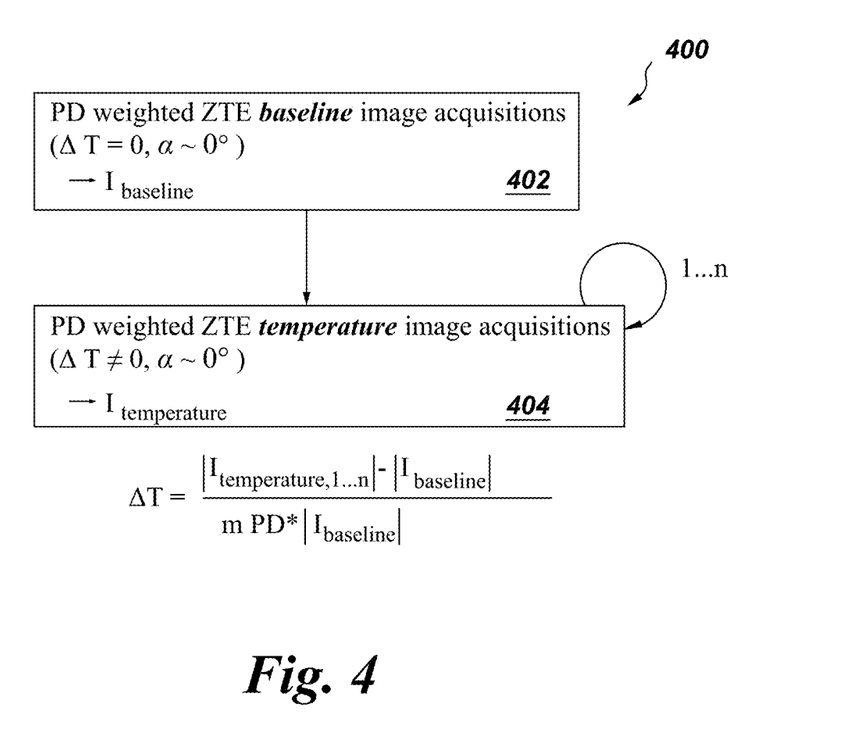
FIG. 4 illustrates one embodiment of the measurement steps when mapping temperature changes based on proton density weighted zero TE imaging.

In FIG. 4, an embodiment of the system 400 measuring the temperature change based on PD weighted ZTE imaging comprises the steps of acquiring PD weighted ZTE baseline images ($I_{baseline}(t_0,\alpha\approx 0)$) at 402 with a low flip angle ($\alpha\approx 0°$) from a single image or set of multiple images before heating or cooling the object of investigation at time $t_0$. A next step comprises acquiring PD weighted ZTE temperature images ($I_{temperature}(t_{1...n},\alpha\approx 0)$) at 404 with low flip angle ($\alpha\approx 0°$) while heating and cooling the object of investigation at multiple time steps (time $t_{1...n}$). Finally, the temperature changes $\Delta T$ over time are extracted by calculating the relative deviations according to:

$$\Delta T = \frac{|I_{temperature}(t_{1...n},\alpha\approx 0)| - |I_{baseline}(t_0,\alpha\approx 0)|}{m_{PD}*|I_{baseline}(t_0,\alpha\approx 0)|} \qquad [8]$$

with the PD temperature coefficient $m_{PD}\approx -0.3\%/°$ C.

Figure 5:
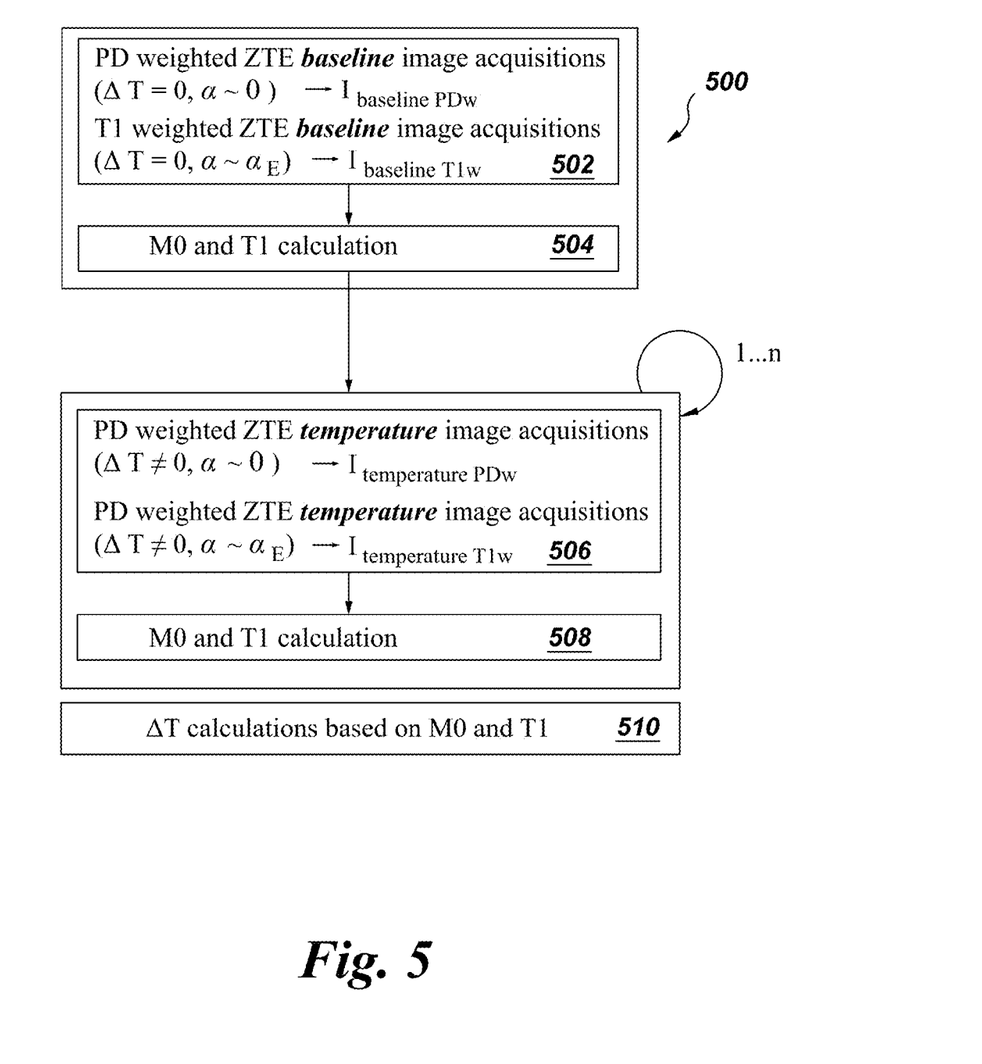
FIG. 5 illustrates the measurement steps when mapping temperature changes based on proton density and T1 weighting zero TE.

As shown in FIG. 5, a system 500 measuring the temperature change based on PD and T1 weighted ZTE imaging comprises the steps of acquiring PD weighted ZTE baseline images ($I_{baseline\_PDw}(t_0,\alpha 1\approx 0)$, called y1($t_0$) in the following text and equations) with low flip angle ($\alpha 1\approx 0°$) and T1 weighted ZTE baseline images ($I_{baseline\_T1w}(t_0,\alpha\approx\alpha_E)$, called y2($t_0$) in the following text and equations) with a flip angle that achieves T1 weighting at 502, for example close to the SNR-optimal Ernst angle ($\alpha_E$). Both baseline images are input to the M0 calculation at 504 according to:

$$M0(t_0) = \frac{y1(t_0)y2(t_0)(\alpha 2^2 - \alpha 1^2)}{\alpha 1\alpha 2(\alpha 2 y2(t_0) - \alpha 1 y1(t_0))}. \qquad [9]$$

In another aspect, both baseline images are input to the T1 calculation at 504 according to:

$$T1(t_0) = \frac{2TR}{\alpha 1 \alpha 2} \frac{(\alpha 2 y1(t_0) - \alpha 1 y2(t_0))}{(\alpha 2 y2(t_0) - \alpha 1 y1(t_0))} \quad [10]$$

These steps can be performed at a single or at multiple time steps before heating or cooling the object of investigation.

A next step comprises acquiring PD weighted ZTE temperature images ($I_{baseline\_PDw}(t_1 \ldots {}_n, \alpha 1 \approx 0)$, called $y1(t_{1 \ldots n})$ in the following text and equations) with low flip angle for PD weighting ($\alpha \approx 0°$) and T1 weighted ZTE temperature images ($I_{baseline\_T1w}(t_1 \ldots {}_n, \alpha \approx \alpha_E)$ called $y2(t_{1 \ldots n})$ in the following text and equations) with a flip angle that achieves T1 weighting at 506, for example close to the Ernst angle ($a_E$). Both temperature images are input to the M0 calculation 508 according to:

$$M0(t_{1 \ldots n}) = \frac{y1(t_{1 \ldots n}) y2(t_{1 \ldots n})(\alpha 2^2 - \alpha 1^2)}{\alpha 1 \alpha 2 (\alpha 2 y2(t_{1 \ldots n}) - \alpha 1 y1(t_{1 \ldots n}))}. \quad [11]$$

In one aspect, both baseline images are input to the T1 calculation 508 according to:

$$T1(t_{1 \ldots n}) = \frac{2TR}{\alpha 1 \alpha 2} \frac{(\alpha 2 y1(t_{1 \ldots n}) - \alpha 1 y2(t_{1 \ldots n}))}{\alpha 2 y2(t_{1 \ldots n}) - \alpha 1 y1(t_{1 \ldots n})}. \quad [12]$$

The temperature images are acquired for multiple time steps while heating or cooling the object of investigation.

Finally, the temperature changes ΔT over time are extracted at 510 by calculating the relative deviations from baseline and temperature dependent M0 and T1. The information of M0 and T1 might be used to correct for inaccuracies and compensate for low SNR.

Figure 6:
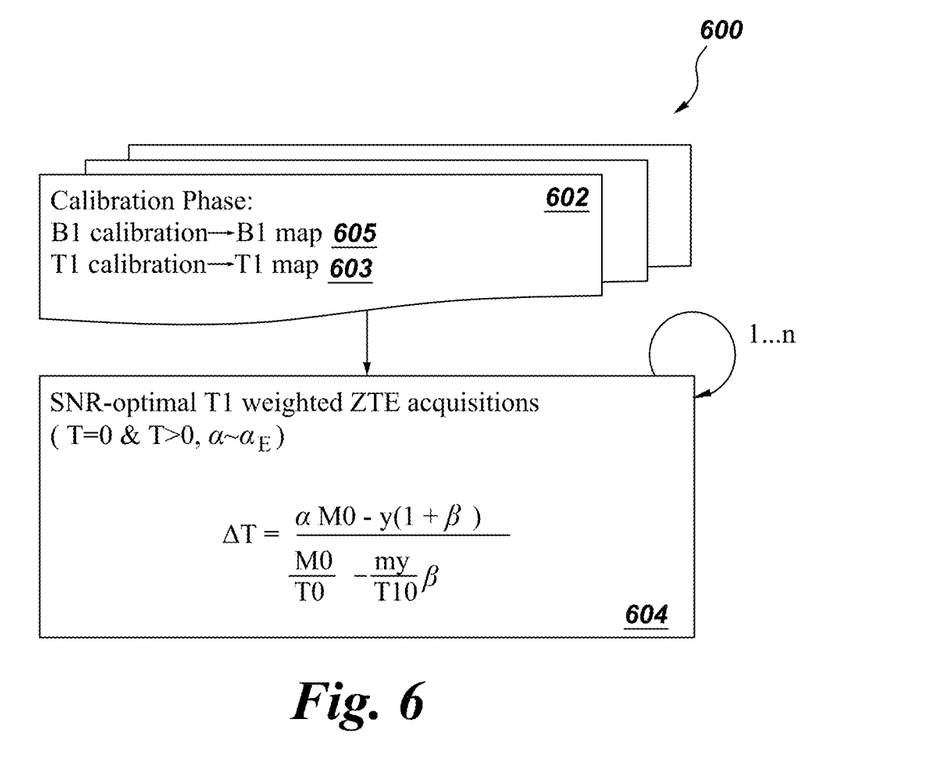
FIG. 6 illustrates the measurement steps when mapping temperature changes based on the signal to noise optimized T1 weighted zero TE imaging with T1 and B1 map calibration.

As shown in FIG. 6, a system 600 measuring the temperature change based on SNR-optimized T1 weighted ZTE imaging comprises a calibration step 602 to acquire a T10 map 603. This calibration step may be based on variable flip angle (VFA) ZTE imaging or any other existing $T_1$ mapping techniques.

A second calibration step is performed to acquire a B1 map 605. This calibration step may be based on VFA ZTE imaging, or any other existing B1 mapping techniques to consider B1 inhomogeneity effects to represent the actual flip angle achieved while measurement. The T10 and B1 calibration map are used to consider the T1 signal contamination in the temperature equation. Before and while heating or cooling the object of investigation, ZTE temperature images with flip angles optimized for T1 contrast (for example, the Ernst angle) at multiple time steps are acquired and the temperature changes ΔT are computed 604 for each time step at once, simultaneously, according to Equation 7.

Optionally, additional T1 and B1 map updates 602 can be acquired during the experiment to further increase accuracy.

The described methods map temperature in the different layers of cortical bone, as well as in aqueous and adipose tissue. Moreover, the temperature mapping can be performed in bone, aqueous tissue, and adipose tissue, simultaneously.

Temperature Changes in Tissue and Bone are Simultaneously Tracked

With the proposed method, temperature changes in different layers of bone, especially cortical bone and various tissues, including adipose tissue, are simultaneously tracked with high spatiotemporal encoding efficiency. The method allows temperature mapping in three-dimensional (3D) space. The method is robust in terms of B0 and chemical shift off-resonance, as well as being insensitive to eddy currents to provide for accurate temperature mapping. The sequence is silent so that a patient's comfort is increased during long treatment sessions. Some of the non-invasive or minimally invasive thermal therapies utilize information about location and geometry of bones within the treatment area, or within the path of the energy transmission. Current therapy planning techniques use co-registered CT images to asses this information. Zero TE may be introduced as a single modality treatment planning method simplifying the overall workflow by eliminating the time consuming extra CT scan acquisition and registration. Zero TE is an overall effective method for PD weighted imaging and high SNR efficiency. The temperature map extraction is very simple such that no phase unwrapping is needed. Furthermore, because of 3D radial sampling, ZTE is robust against motion. Additionally, the T1 contamination of PD weighted signal is directly calibrated using T1 weighted ZTE instead of analytically calculating the effect.

Relative Temperature Changes in Tissue and Bone

An embodiment of the system 400 is demonstrated by experiments performed on a fresh beef shank 702 cooled to ~1.5° C. The warm-up of the beef shank was tracked using the proposed PD weighted ZTE pulse sequence (See FIG. 7). For this experiment scan the following scan parameters were used: FOV=26 cm^3, resolution=3 mm^3, FA=1 deg, TR=1 ms, number of averages=4, imaging bandwidth=±62.5 kHz, scan time=23 s.

Figure 7:
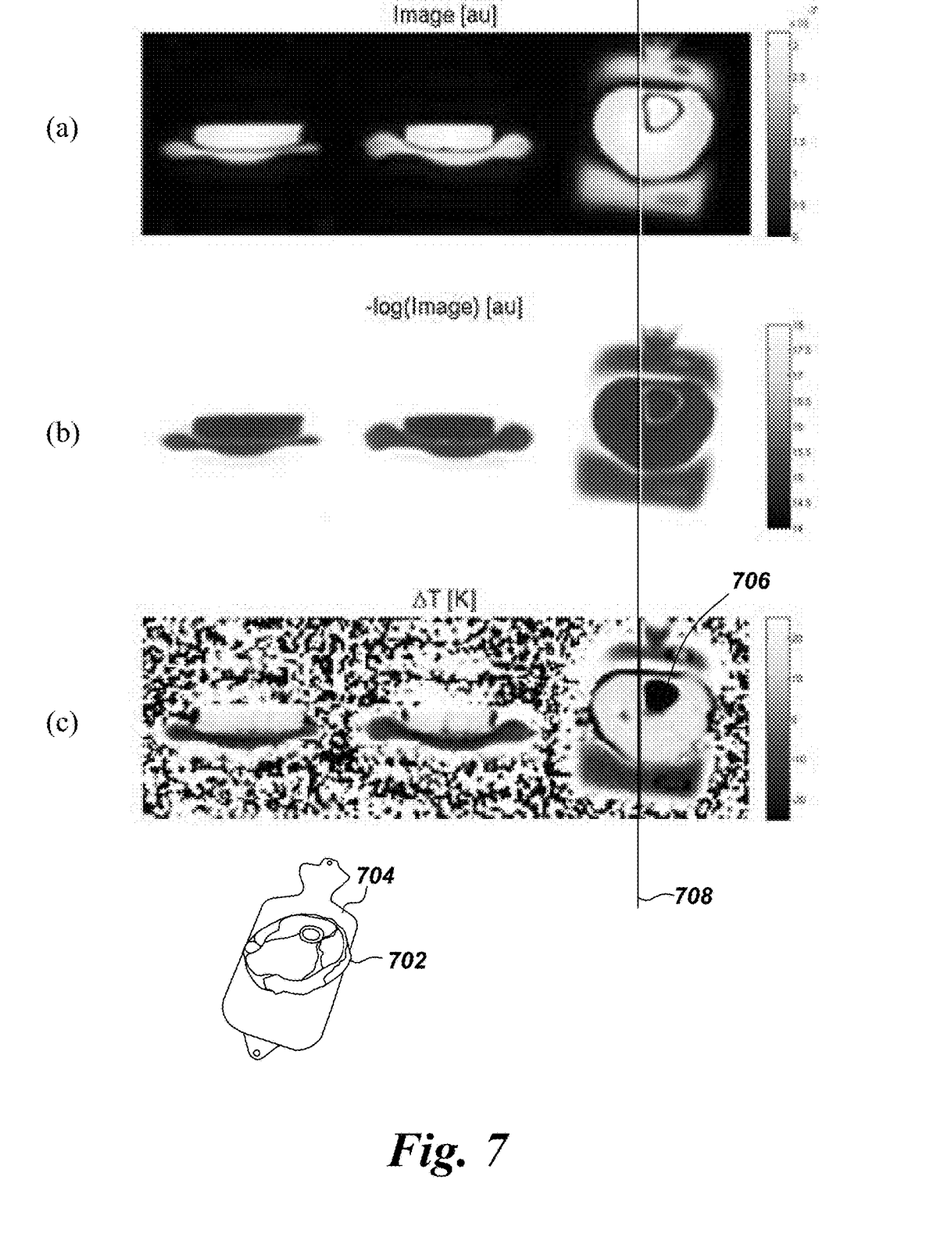
FIG. 7 depicts an embodiment of orthogonal slices of ZTE image in (a) linear scale; (b) log scale; and (c) the temperature after a duration of time.

The beef shank 702 was additionally heated by placing it on top of a hot water bag 704. An SNR of about 300 was achieved and resulted in about 1° C. temperature accuracy. Images were acquired every 2 min for 30 minutes. The temperature change ΔT at 30 minutes was evaluated according to Equation 8.

FIG. 7 shows three orthogonal ZTE slices of the beef shank 702 surrounded by a hot water bag 704 in (a) linear scale (top) and (b) log scale (middle). The bottom row (c) depicts a temperature increase after about 30 minutes (starting at about 5° C.). An approximate +20° C. temperature change is detected which is based on the fact that the beef shank gets warmer, whereas the water bag cools down. The black hole 706 in the temperature map is related to bone marrow decomposition in response to freezing/heating. The vertical line indicates the location of cortical bone 708 in the three subplots.

Another experiment was performed with a heating pack (~38° C.) positioned at a volunteer's forehead (surface temperature ~34° C.). For this experiment the following scan parameters were used: FOV=22 cm^3, resolution=2.8 mm^3, slices=72, FA=1 deg, TR=1 ms, number of averages=1, imaging bandwidth=±62.5 kHz, scan time=18 s. Zero TE images were acquired for about 20 minutes.

Two initial scans were performed without heating pack, 20 scans performed with the heating pack, and 16 scans performed after the pack was removed again. Motion of the head between the acquisitions was detected influencing the accuracy of ΔT. Image registration was applied to correct for these displacements and SNR efficiency could be increased from ~99 to ~106.

In order to enable real time temperature mapping, image acquisitions can be combined with temporal acceleration methods including sliding window reconstruction, view sharing, parallel imaging, compressed sensing, regularization methods, and sparse and low rank reconstruction, alone or in combination. Another method to speed up image acquisition is to utilize the undersampling capabilities of 3D radial imaging allowing the selection of smaller field of views i.e. for focal imaging.

In order to compensate for motion artifacts, image acquisitions can be combined with motion compensation and correction approaches such as image registration and gated or triggered data acquisition.

Transcranial magnetic resonance (MR) guided focused ultrasound (tcMRgFUS) has become a promising technology for non-invasive treatment of brain diseases. In tcMRgFUS, the cranium absorbs energy while sonication and heat is created. Phase aberration correction is needed for tcMRgFUS treatment planning and the skull is additionally cooled during sonication. One key goal for tcMRgFUS is to extract temperature changes inside the sonication hot-spot inside the brain as well as in the skull with a high spatiotemporal resolution. The method as described provides capabilities in using ZTE and ZTE based temperature mapping in tcMRgFUS for (i) treatment planning as described and simultaneous temperature monitoring in bone and cerebral tissue.

Another application provides for the treatment of bone metastases using focused ultrasound, where currently soft tissue near bone is monitored and interpolations are made on temperature changes in bony structures. Other scenarios could also involve treatments where bone is in the path of for example the ultrasound beam (i.e. spine). Applying the proposed method enables a save monitoring of heat produced in bone due to energy absorption.

The method is not limited to focused ultrasound based treatments, but also is applicable for MR based temperature mapping using RF hyperthermia or laser ablation or other relevant thermal therapy modalities.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

The invention claimed is:

1. A method of mapping and tracking temperature changes using magnetic resonance imaging (MRI) of MRI-visible tissues by leveraging the effect of proton density (PD) and longitudinal relaxation time (T1) weighting including T1 and radio frequency field strength (B1) correction to perform temperature mapping, the method comprising the steps of:
   generating a plurality of images with PD and T1 weighting by adjusting flip angles and repetition times (TR) to produce a series comprising one or more PD weighted images, PD and T1 weighted images, and signal-to-noise (SNR)-optimized T1 weighted images that are indicative of temperature information within different layers of MRI-visible tissues;
   calibrating T1 signal contamination from the series comprising the one or more PD weighted ZTE images, PD and T1 weighted images, and signal-to-noise (SNR)-optimized T1 weighted images; and
   extracting temperature changes from the series comprising the one or more PD weighted images, PD and T1 weighted images, and signal-to-noise (SNR)-optimized T1 weighted images to map and track temperature changes in the MRI-visible tissues.

2. The method of claim 1, wherein the step of generating a plurality of images, the images are acquired with zero echo time (ZTE) acquisitions.

3. The method of claim 1, wherein the step of calibrating T1 signal contamination comprises the steps of determining a T1 calibration map from a T1 monitoring region of interest, re-calibrating the T1 calibration map and repeatedly updating the T1 calibration map by applying a T1 mapping sequence.

4. The method of claim 3, wherein the T1 mapping sequence is a zero echo time (ZTE) pulse sequence based variable flip angle (VFA) calibration method that produces one or more of the series.

5. The method of claim 3, wherein the step of calibrating T1 signal contamination comprises the steps of determining a B1 calibration map, re-calibrating the B1 calibration map, and repeatedly updating the B1 calibration map by applying a B1 mapping sequence.

6. The method of claim 5, wherein the B1 mapping sequence is a ZTE pulse sequence based variable flip angle (VFA) calibration method that produces one or more of the series.

7. The method of claim 1, further comprising a thermal equilibrium magnetization M0 greater than about 90%.

8. The method of claim 1, wherein the MRI-visible tissues include bone, aqueous and adipose tissues.

9. The method of claim 1, wherein the step of extracting temperature changes, the MRI-visible tissues include bone compositions comprising bone marrow, cortical bone, and trabecular bone.

10. The method of claim 1, further comprising a step of correcting for motion using image registration and self-gating.

11. The method of claim 1, further comprising temporal acceleration methods including sliding window reconstruction, view sharing, parallel imaging, compressed sensing, regularization methods, focal imaging, sparse and low rank reconstruction, alone or in combination.

12. The method of claim 2, wherein the step of generating the plurality of ZTE pulse sequences is based on image acquisition performed in three dimensional (3D) space.

13. The method of claim 2, where step of generating a plurality of ZTE pulse sequences is performed silently.

14. The method of claim 2, wherein the step of generating a plurality of ZTE sequences is insensitive to geometric distortions and eddy currents to accurately map temperature in the MRI-visible tissues.

15. The method of claim 1, further comprising steps of implementing thermal therapy guidance techniques.

16. The method of claim 15, wherein the thermal therapy guidance techniques include methods of hyperthermia comprising radiofrequency (RF) ablation, laser ablation, high-intensity focused ultrasound (HIFU), infrared, microwave, magnetic and induction heating.

17. The method of claim 15, wherein the thermal therapy guidance techniques include methods of cryotherapy comprising passive and active cooling therapies such as cryo-ablation.

* * * * *